US008728750B2

(12) United States Patent
Robins et al.

(10) Patent No.: US 8,728,750 B2
(45) Date of Patent: May 20, 2014

(54) PROCESS FOR PREPARATION OF OPTICALLY ACTIVE N-PROTECTED 3-AMINOPYRROLIDINE OR OPTICALLY ACTIVE N-PROTECTED 3-AMINOPIPERIDINE AND THE CORRESPONDING KETONES BY OPTICAL RESOLUTION OF THE RACEMIC AMINE MIXTURES EMPLOYING A BACTERIAL OMEGA-TRANSAMINASE

(75) Inventors: Karen Robins, Visp (CH); Uwe Bornscheuer, Greifswald (DE); Matthias Höhne, Bandelin (DE)

(73) Assignee: Lonza AG, Visp (CH)

( * ) Notice: Subject to any disclaimer, the term of this patent is extended or adjusted under 35 U.S.C. 154(b) by 807 days.

(21) Appl. No.: 12/438,674

(22) PCT Filed: Sep. 6, 2007

(86) PCT No.: PCT/EP2007/007770
§ 371 (c)(1),
(2), (4) Date: Feb. 24, 2009

(87) PCT Pub. No.: WO2008/028654
PCT Pub. Date: Mar. 13, 2008

(65) Prior Publication Data
US 2009/0325224 A1    Dec. 31, 2009

(30) Foreign Application Priority Data
Sep. 6, 2006  (EP) ..................................... 06018637

(51) Int. Cl.
*C12Q 1/52* (2006.01)
*C12P 1/00* (2006.01)

(52) U.S. Cl.
USPC ............................................. 435/16; 435/41

(58) Field of Classification Search
None
See application file for complete search history.

(56) References Cited

U.S. PATENT DOCUMENTS

2010/0285544 A1* 11/2010 Ito et al. .................... 435/128

FOREIGN PATENT DOCUMENTS

| EP | 0 404 146 | | 12/1990 | |
|---|---|---|---|---|
| JP | WO/2006/126498 | * | 5/2006 | ............. C12N 15/09 |
| WO | WO-95/13069 A | | 5/1995 | |
| WO | WO-2006/009869 A | | 1/2006 | |

OTHER PUBLICATIONS

Definition of bearing (last viewed on Oct. 31, 2011).*
Structure of 1-Boc-3-aminopyrrolidine (last viewed on Oct. 28, 2011).*
Structure of 3-pyrrolidone (last viewed on Nov. 1, 2011).*
Vargas-Sanchez et al., 3-aminopyrrolidines via Ring Rearrangementof 2-aminomethylazetidines. Synthesis of (−)-Absouline, Organic Letters, 2005, vol. 7, pp. 5861-5864.*
Coffey et al., Large Scale Deprotection of a tert-Butoxycarbonyl (Boc) Group Using Aqueous HCl and Acetone, Organic Process Research & Development, 2004, vol. 8, pp. 945-947.*
Salvatore et al., Synthesis of secondary amine, Tetrahedron, vol. 57, pp. 7785-7811.*
Taylor et al. (Novel biosynthetic approaches to the production of unnatural amino acids using transaminases, Trends in Biotechnology, vol. 16, Issue 10, Oct. 1, 1998, pp. 412-418.*
Cho et al., Simultaneous synthesis of enantiomerically pure (S)-amino acids and (R)-amines using coupled transaminase reactions Biotechnology and Bioengineering, vol. 81, Issue 7, pp. 783-789, Mar. 30, 2003.*
Shin, J. S. & Kim, B. G.: "Exploring the Active Site of Amine: Pyruvate Aminotransferase on the Basis of the Substrate Structure-Reactivity Relationship: How the Enzyme Controls Substrate Specificity and Stereoselectivity," Journal of Organic Chemistry, vol. 67, No. 9, May 2002, pp. 2848-2853, XP002420352.
Cho, B. K. et al.: "Simultaneous synthesis of enantiomerically pure (S)-amino acids and (R)-amines using alpha/omega-aminotransferase coupling reactions with two-liquid phase reaction system," Journal of Molecular Catalysis B: Enzymatic, vol. 26, No. 3-6, Dec. 2003, pp. 273-285, XP002420351.
Shin, J.S. & Kim, B.G.: "Comparison of the omega-Transaminases from Different Microorganisms and Application to Production of Chiral Amines," Bioscience Biotechnology Biochemistry, vol. 65, No. 8, Aug. 2001, pp. 1782-1788, XP009010899.
Yun, H. et al: "omega-Amino Acid: Pyruvate Transaminase from *Alcaligenes denitrificans* Y2k-2: a New Catalyst for Kinetic Resolution of beta-Amino Acids and Amines," Applied and Environmental Microbiology, vol. 70, No. 4, Apr. 2004, pp. 2529-2534, XP009029815.
Yun, H. et al.: "Simultaneous synthesis of enantiomerically pure (R)-1-phenylethanol and (R)-alpha-methylbenzylamine from racemic alpha-methylbenzylamine using omega-transaminase/alcohol dehydrogenase/glucose dehydrogenase coupling reaction," Biotechnology Letters, vol. 25, No. 10, May 2003, pp. 809-814, XP002420353.
Shin, J.S. et al.: "Kinetic Resolution of Chiral Amines with omega-Transaminase Using an Enzyme-Membrane Reactor," Biotechnology and Bioengineering, vol. 73, No. 3, May 2001, pp. 179-187, XP002420354.
Amine and Alcohol charts retrieved from URL http://www.ecompound.com/Reactionreference/common_protection_group.htm on Jun. 14, 2012, Copyright 2005-2006.
Daley, et al., "Organic Chemistry," Chapter 15, Jul. 5, 2005, pp. 769-782.
Green, et al., Functional Groups: Amino Protecting Groups Stability, retrieved from URL: www.organic-chemistry.org/protectivegroups/amino.shtm o Jun. 14, 2012, Wiley-Interscience, New York, 1999.
Greene, et al., "The Role of Protective Groups in Organic Synthesis," Protective Groups in Organic Synthesis, Third Edition, pp. 1-16, Copyright 1999.

* cited by examiner

*Primary Examiner* — Alexander Kim
(74) *Attorney, Agent, or Firm* — Harness, Dickey & Pierce, P.L.C.

(57) ABSTRACT

The present invention relates to the production of optically active amines, which can be used as intermediate products in a synthesis of for instance pharmaceutical products.

14 Claims, No Drawings

PROCESS FOR PREPARATION OF OPTICALLY ACTIVE N-PROTECTED 3-AMINOPYRROLIDINE OR OPTICALLY ACTIVE N-PROTECTED 3-AMINOPIPERIDINE AND THE CORRESPONDING KETONES BY OPTICAL RESOLUTION OF THE RACEMIC AMINE MIXTURES EMPLOYING A BACTERIAL OMEGA-TRANSAMINASE

CROSS-REFERENCE TO RELATED APPLICATIONS

This application is a 371 U.S. National Stage of International Application No. PCT/EP2007007770, filed Sep. 6, 2007 and published in English as WO 2008/028654 A1 on Mar. 13, 2008. This application claims priority to European Patent Application No. EP 06018637.6, filed Sep. 6, 2006, which application is herein expressly incorporated by reference.

The present invention relates to a process for the preparation of optically active chiral amines.

Chiral amines play an important role in the pharmaceutical, agrochemical and chemical industry. They are frequently used as intermediates or synthones for the preparation of various physiologically, for instance pharmaceutically active substances, such as cephalosporine or pyrrolidine derivatives. In a great number of the various applications of chiral amines, only one particular optically active form, either the (R) or the (S) enantiomer is physiologically active. Thus, there is a clear need to provide processes for the preparation of chiral amines in an optically active form.

These needs are partially met by preparing chiral amines by crystallisation of diastereomeric salts through adding of chiral carboxylic acids (Breuer et al., Angewandte Chemie (2004) 116, 806-843). Other chemical methods use enantioselective synthesis by reducing prochiral precursors with C=N-double bonds.

Furthermore, it is known to stereoselectively cleave racemates using various enzymes, such as proteases, amidases or lipases (Bornscheuer and Kazlauskas, Hydrolases in Organic Synthesis (2005), Wiley-VCH Weinheim). It is also known that specific transaminases, namely α-transaminases, are suitable for the preparation of optically active amino acids (Bartsch et al., Appl. Environm. Microbiol. (1996) 62, 3794-3799, Cho et al., Biotechnol. Bioeng. (2003) 83, 226-234, JP 011 53084 A2 (1998), JP 633 04986 A2 (1988), EP 0 248 357 A2 and Ziehr et al., Biotechnol. Bioeng. (1987) 29, 482-487).

However, these prior art processes suffer from various disadvantages. Although the enzymatic processes usually employ in contrast to the classical methods favourable mild conditions and achieve a reasonable stereoselectivity, they regularly use enzymes, whose substrate specificity, enantioselectivity and/or conversion are not sufficiently high for industrially applicable processes. Furthermore, one of the most prominent drawbacks of using transaminases for the preparation of optically active amines is represented by the frequently observed substrate and product inhibition phenomena. It is therefore one of the objects of the present invention to provide an improved process for preparing optically active chiral amines, in particular a process with an improved substrate specificity, an improved conversion and/or an improved enantioselectivity.

The present invention solves the underlying technical problem by providing a process for the preparation of an optically active chiral amine, said process comprising reacting an amino acceptor compound comprising a keto group and a racemic mixture of 3-aminopyrrolidine (3AP) or 3-aminopiperidine (3APi), each bearing a protective group at the ring nitrogen atom in the presence of a (R)- or (S)-selective transaminase to obtain one enantiomer of 3AP or 3APi, the amino compound corresponding to said amino acceptor compound, and N-protected pyrrolidine-3-one or N-protected piperidine-3-one as ketone product.

The process of the present invention comprises (a) providing an amino acceptor and a racemic mixture of 1-N-protected 3AP or 1-N-protected 3APi, i.e. a mixture of the two enantiomers of the respective amine, (b) reacting the amino acceptor and the racemic mixture of the respective amine with a (R)- or (S)-selective transaminase, and (c) obtaining an optically active chiral amine, an amino product and a ketone product.

According to a preferred embodiment of the present invention, in a subsequent further optional process step, the optically active chiral amine obtained in step c) is isolated and purified from the reaction mixture obtained in step c).

The reaction of the present invention follows in principle the following scheme:

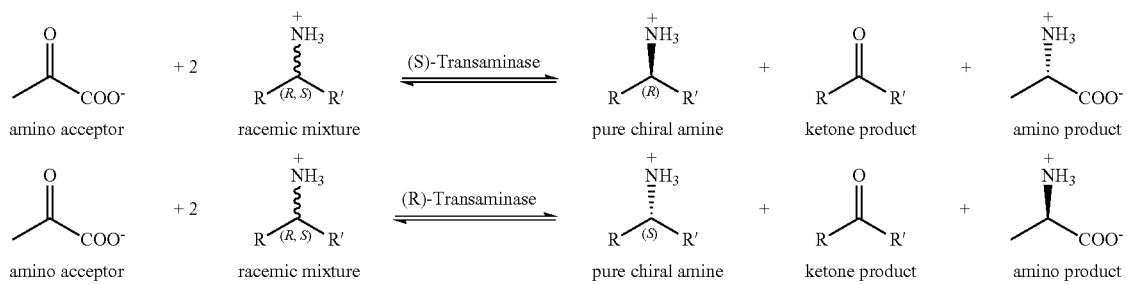

According to the present invention the racemic mixture of 3-aminopyrrolidine (3AP) or the racemic mixture of 3-aminopiperidine (3APi) bears a protective group at the secondary nitrogen atom of the ring, i.e. at position 1 whereas the amino group at the chiral centre of the amine, i.e. position 3, that participates in the transamination is not protected.

The presence of the protective group causes that the protected amine, i.e. 1-N-protected 3AP or 1-N-protected 3APi, is converted more efficiently to the desired optically active chiral amine. Thus the presence of the protective group causes that higher yields of the desired optically active chiral amine are obtained. In comparison to that the conversion of the starting amine without a protective group at the ring nitrogen atom is less efficient.

Thus, the present invention provides a process for the enzymatic cleavage of 1-N-protected amines by using at least one (R)- or (S)-selective transaminase for the transamination of an amino group from one specific enantiomer of the mixture of the 1-N-protected chiral amine enantiomers to an amino acceptor, thereby forming the desired optically active product. In the context of the present invention the terms "enzymatic cleavage of amines" or "enzymatic cleavage of a racemic mixture" shall mean the optical resolution of a racemic mixture by stereoselective enzymatic transformation of one enantiomer. Depending on the enantiopreference of the specific (R)- or (S)-selective transaminase used, an optically active chiral amine of the desired optical configuration, i.e. either the (R) or (S) enantiomer, is obtained. Thus, using in one embodiment of the present invention a (S)-selective transaminase for the enzymatic cleavage synthesis eliminates the (S) enantiomer from the racemic mixture and generates the desired optically active (R) enantiomer of the chiral amine while using in another embodiment of the present invention an (R)-selective-transaminase eliminates the (R) enantiomer from the racemic mixture and generates the desired optically active (S) enantiomer. In addition to the desired optically active chiral amine the reaction produces a ketone product from the transamination of the racemic mixture, an amino product from the used amino acceptor and partially non-cleaved undesired enantiomer as well as unconverted amino acceptor.

In a preferred embodiment of the present invention the protective group is a tert-butoxycarbonyl (Boc) group. In another preferred embodiment the protective group is a benzyl group. In still another preferred embodiment the protective group is a carbobenzoxy—also called benzyloxycarbonyl—(Cbz) group.

In the context of the present invention, a transaminase is a pyridoxalphosphate-dependent enzyme catalysing the transfer of amino groups. Transaminases are classified in E.C. 2.6.1.X. In a particularly preferred embodiment of the present invention, the transaminase is an (R)- or (S)-selective transaminase, particular is in a preferred embodiment an ω-transaminase.

In the context of the present invention an (R)- or (S)-selective transaminase is an enzyme with the classification code E.C.2.6.1.18. These amino transaminases are characterised in that they mainly use primary amines as substrates. These enzymes are further characterised by exhibiting an equilibrium constant of (R)- or (S)-selective transaminase catalysed reactions which is greater than 1. (R)- or (S)-selective transaminases which may be used according to the present invention are described for instance in Iwasaki et al., Biotechnol. Lett. (2003) 25, 1843-1846, Shin et al., Biotechnol. Bioeng. (1997) 55, 348-358, Shin and Kim, Book of Abstracts, 217$^{th}$ ACS National Meeting, Anaheim, Calif., Mar. 21-25, (1999) 180, Shin and Kim, Biosc. Biotechnol. Biochem. (2001) 65, 1782-1788 and Shin and Kim, Biotechnol. Bioeng. (1998) 60, 534-540.

Thus, in a preferred embodiment of the present invention, the (R)- or (S)-selective transaminase used in the present process is an (R)- or (S)-selective transaminase obtained from *Vibrio fluvialis*, in particular from strain JS17, *Alcaligenes denitrificans*, in particular from strain Y2k-2, *Klebsiella pneumoniae*, in particular from strain YS2F or *Bacillus thuringiensis*, in particular from strain JS64 (for the strain designations see Shin and Kim, 1998, above). Of course the present invention also understands under the term (R)- or (S)-selective transaminase an extract of an organism, such as a microorganism or a cell, containing an (R)- or (S)-selective transaminase or a living or dead cell or microorganism itself comprising an (R)- or (S)-selective transaminase. Such a microorganism or cell or extract or transaminase enzyme may be used in immobilised or non-immobilised form. The (R)- or (S)-selective transaminase may also be a recombinantly produced naturally occurring or genetically modified (R)- or (S)-selective transaminase, which is coded partially or completely by a nucleic acid sequence or a derivative thereof contained in one of the above-identified organisms or being equivalent thereto.

In the context of the present invention the term optically active chiral amine relates to the same subject-matter as the term enantiomerically active chiral amine. These terms in particular refer to a preparation which is essentially free, in an even more preferred embodiment free of the undesired enantiomer. Accordingly, an optically active chiral amine essentially comprises an excess of one enantiomer or even consists of only one enantiomer.

In particular, in the context of the present invention, an optically active chiral amine has an optical purity of at least 70, 80, 90, 91, 92, 93, 94, 95, 96, 97, 98, 99, 99.5, 99.6, 99.7, 99.8 and in particular at least 99.9%.

In the present invention the optical purity is given in % excess of one enantiomer over the other enantiomer. Thus, the optical purity in % is the quotient of the difference between the (R) and the (S) enantiomer concentrations and the sum of the concentrations of both enantiomers (optical purity of A in %=([A]−[B]):([A]+[B])×100, wherein A and B represent the concentrations of the (R) and (S) enantiomers or vice versa).

In the present invention it is preferred that the racemic mixture of the chiral amine is converted to the desired optically active chiral amine in a degree of conversion of at least 30, 40, 45, 46, 47, 48, 49, in particular 50%. The concentrations for analysing the optical purity and the conversion can be determined for instance using HPLC, gaschromatography (GC) or photo- or fluorimetric methods.

According to the present invention it could be shown that the protective group has a positive effect on the conversion rate and thus leads to an elevated yield of (R)-3-aminopyrrolidine using a (S)-specific transaminase. Furthermore, the protective group showed also an although less pronounced—effect on the conversion rate of 3-aminopiperidine and exerted a positive effect on the selectivity of the enzyme.

In the context of the present invention an amino acceptor is a molecule containing a keto group and capable of accepting an amino group transferred from an amino donor, i.e. in the present case from an amine of a racemic mixture of amines, by an (R)- or (S)-selective transaminase. In a particularly preferred embodiment of the present invention the amino acceptor is an α-keto acid. In an even more preferred embodiment of the present invention the amino acceptor is selected from the group consisting of phenylpyruvic acid, a salt thereof, pyruvic acid, a salt thereof, glyoxylic acid, a salt thereof, acetophenone, 2-ketoglutaric acid, a salt thereof, acetone, 3-oxobutyric acid, a salt thereof and 2-butanone. Furthermore, 3-oxopyrrolidine (3-OP), (3-pyridyl)methylketone (3-PMK), 3-oxobutyric acid ethyl ester (3-OBEE) or 3-oxopentanoic acid methyl ester (3-OPME) can, in a further embodiment of the present invention, also be used as amino acceptors.

According to the invention the amino product obtained by the conversion of the amino acceptor phenylpyruvic acid is phenylalanine. The amino product obtained by the conversion of the amino acceptor pyruvic acid is alanine. The amino product obtained by the conversion of the amino acceptor glyoxylic acid is glycine. The amino product obtained by the conversion of the amino acceptor acetophenone is 1-phenylethylamine. The amino product obtained by the conversion of the amino acceptor 2-ketoglutaric acid is glutamic acid. The amino product obtained by the conversion of the amino acceptor acetone is isopropylamine. The amino product obtained by the conversion of the amino acceptor 3-oxobutyric acid is 3-aminobutyric acid. The amino product obtained by the conversion of the amino acceptor 2-butanone is sec-butylamine. The amino product obtained by the conversion of the amino acceptor 3-oxobutyric acid ethyl ester (3-OBEE) is 3-aminobutyric acid. The amino product obtained by the conversion of the amino acceptor 3-oxopentanoic acid methyl ester (3-OPME) is 3-aminopentanoic acid methyl ester.

The obtained desired optically active chiral amine is therefore in a preferred embodiment dependent upon the used (R)- or (S)-selective transaminase either the (S) or the (R) enantiomer of said chiral amine.

According to the invention the ketone product obtained by the present process is 1-N-protected pyrrolidine-3-one or 1-N-protected piperidine-3-one.

The process of the present invention comprises the reaction of a racemic mixture of 1-N-protected 3-aminopyrrolidine (3AP) with an (S)- or (R)-selective-transaminase and an amino acceptor to obtain optically active (R) or (S) 1-N-protected 3AP. The inventive process also comprises the reaction of a racemic mixture of 1-N-protected 3-aminopiperidine (3APi) with an (R)- or (S)-selective transaminase and an amino acceptor to obtain optically active (S) or (R) 1-N-protected 3APi.

According to the process of the present invention the protective group of the obtained 1-N-protected 3AP or 1-N-protected 3APi can be removed by any deprotection method known in the art for the removal. A method for the removal of tert-butoxycarbonyl (Boc) group using concentrated HCl and acetone is for example described by Coffey et al., Org. Proc. Res. Dev., 8 (6) (2004), pages 945-947.

In a particularly preferred embodiment of the present invention, the amino acceptor and the racemic mixture of amines are reacted with the transaminase in aqueous medium, for example physiological buffer. In a particularly preferred embodiment the transamination reaction is carried out at a pH in the range from 5 to 9, in particular from 7 to 8.5. In a particular preferred embodiment, the reaction is carried out in a temperature range from 10 to 65° C., preferably 20 to 50° C., in particular 18 to 25° C., preferably room temperature or 34 to 39° C., in particular 37° C. In a further preferred embodiment of the present invention the amino acceptor and the racemic mixture of amines are provided in a molar ratio from 1:1 to 1:10, in particular from 1:1 to 1:4. In a preferred embodiment of the present invention the enzymatic activity may be from 1 to 20.000 μmol/min.

In a particularly preferred embodiment, the present invention relates to a process for the preparation of an optically active chiral amine according to the above, that means according to which in a first process step a) an amino acceptor and racemic mixture of 3-aminopyrrolidine (3AP) or 3-aminopiperidine (3APi), each bearing a protective group at the ring nitrogen atom are provided, in a second process step b) the racemic mixture of the chiral amine and the amino acceptor are reacted with at least one ω-transaminase, in a third process step c) an optically active chiral amine, an amino product and a ketone product are obtained, and wherein in a further process step d) the ketone product and/or amino product obtained in step c) is or are removed from the obtained reaction mixture, in particular removed by reaction with an enzyme, that means by enzymatic cleavage, in particular using an enzyme selected from the group consisting of a decarboxylase, a synthase or a dehydrogenase.

In a further preferred embodiment the ketone and/or amino product may be removed by evaporation or extraction. In a further preferred embodiment the obtained ketone product may be removed by spontaneous decarboxylation.

In a further preferred embodiment, the ketone product obtained in step c) is removed by reaction with an alcohol dehydrogenase (ADH), for example a Lactobacillus kefir ADH, which preferably reduces acetophenon to 1-phenylethanol.

In a further preferred embodiment of the present invention the ketone and/or amino product obtained in step c) is continuously removed from the reaction mixture, preferably by a continuous extraction.

In a particularly preferred embodiment the ketone product may be removed by the use of a two-phase system or an enzyme-membrane reactor by continuous extraction.

These particularly preferred embodiments provide the advantage of obtaining the desired conversion, since the ketone product as byproduct of the present process is removed from the equilibrium reaction. The reaction is forced in direction of the products, thereby providing with a high stereoselectivity a conversion into the desired products. The removal of the ketone product is in particular useful as it minimizes product inhibition.

Further preferred embodiments of the present invention are the subject-matter of sub claims.

The present invention is illustrated in more detail in the following examples.

EXAMPLE 1

Enzymatic Cleavage of (R,S)-B3AP

For the present example an (S) ω-transaminase from *Vibrio fluvialis* (Julich Chemical Solutions, Germany), in the following termed TA7, and an (S) ω-transaminase from *Alcaligenes denitrificans* (Julich Chemical Solutions, Germany), in the following termed TA8, were used in the reaction mixture in a final concentration of 4 U/ml in 50 mM Tris-HCl, pH 7. A solution of a racemic mixture of 10 mM (final concentration) (R,S)-B3AP (N-1-boc-aminopyrrolidine) (20 μmol) was used as educt and reacted in the reaction mixture at 37° C. for 15 hrs with TA7 or TA8 using pyruvate in a final concentration of 10 mM as amino acceptor.

After 15 hrs reaction time (S) ω-transaminase TA7 led to an optical purity of the obtained optically active amine (R)-B3AP of 62.5+/−0.5% in a conversion of 39.0+/−5%.

(S) ω-transaminase TA8 led after 15 hrs reaction time to an optical purity of the obtained optically active (R)-B3AP of 97.5+/−0.5% in a conversion of 47.6+/−5%.

It is evident that the optical purities obtained are high or even very high and are close to values to be expected for an ideal stereoselective enzyme. It is to be noted that for TA7 the optical purity is comparatively lower most likely due to the lower conversion.

EXAMPLE 2

Enzymatic Cleavage of (R,S)-1-N-Boc-3-aminopiperidine

For the enzymatic cleavage of a racemic mixture of (R,S)-1-N-Boc-3-aminopiperidine (final concentration: 10 mM) with pyruvate as amino acceptor (final concentration: 10 mM); (S) ω-transaminase TA8 was used in 50 mM sodium phosphate buffer, pH 7.5. At an enzyme concentration of 2 U/ml of TA8 the optical purity of the obtained optically active (R)-1-N-Boc-3-aminopiperidine of 70+/−0.5% was reached after 72 hrs reaction time at 37° C. in a conversion of 54+/−

5%. Using 20 U/ml of TA8 at the same reaction conditions led to an optical purity of the obtained (R)-1-N-Boc-3-aminopiperidine of 98.5+0.5% in a conversion of 72+/−5%.

EXAMPLE 3

Preparation of Optically Active (R)-B3AP Via Racemic Cleavage 230 mg (0.85 mmol) racemic (R,S)-B3AP was used in a final concentration of 10 mM with 0.8 U/ml (S) ω-transaminase TA8. Pyruvate in a final concentration of 10 mM was used as amino acceptor. The reaction was carried out at pH 8 with 50 mM potassium phosphate buffer at a temperature of 37° C. The excess of enantiomers was determined by gas chromatography. After 7 hrs reaction time the optical purity of the obtained 89.4 mg optically active (R)-B3AP was 98.7+/−0.5% with a yield of 39+/−5% (0.33 mmol).

After completion of the reaction, the pH value was adjusted with 5 N HCl at pH 5. The formed B3OP was extracted four times, each time with 75 ml dichloromethane. Thin-layer chromatography did not detect any B3OP in the reaction solution. Subsequently, the pH-value was adjusted with KOH-solution at pH 13 and extracted three times with each 100 ml dichloromethane. Only one lane with B3AP could be detected in thin layer chromatography. The organic phases containing B3OP and B3AP were unified, dried with water-free sodium sulphate and subsequently the solubilising agent was evaporated. Thereafter, $^1$H and $^{13}$C-NMR-spectra (300 MHz) were taken.

103.6 mg Boc-3-pyrrolidinone corresponding to a conversion of 44+/−5% was obtained as ketone product. In addition, the amino product alanine was obtained. Selectively removing the amino product alanine, for instance by enzymatic reaction with an alanine dehydrogenase, proves useful as it minimizes product inhibition caused by the generated alanine, which in turn could be used in order to use higher concentrations of the amine as educt. The same holds true for the use of acetone.

The conversion rate may be increased by using as amino acceptor acetone, which may—after having been converted into the amino product isopropylamine—be removed under reduced pressure from the reaction product.

EXAMPLE 4

Optical Resolution of a Racemic Mixture of 1-N-benzyl-3-aminopyrrolidine (Be3AP) with *Vibrio fluvialis* Transaminase A 1.5 ml reaction vial was charged with:
10 μl of a (R,S)-Be3AP solution in DMSO (5 mM final concentration)
20 μl pyridoxal phosphate, 10 mM (0.2 mM final concentration)
100 μl pyruvate, 100 mM (10 mM final concentration)
830 μl of a sodium phosphate buffer, 50 mM, pH 8

The reaction was started by the addition of 40 μl *Vibrio fluvialis*-transaminase. This corresponds to 7 U/ml. After 0 min, 10 min, 30 min and 60 min samples were taken.

The progress of the reaction and the optical purity is given in Table 1.

| Time [min] | Enantiomeric excess of (R)-Be3AP [% ee$_R$] | Concentration of Be3AP [mM] | Conversion [%] |
|---|---|---|---|
| 0 | 0 | 5 | 0 |
| 10 | 63 | 2.3 | 54 |
| 30 | 96 | 1.55 | 69 |
| 60 | 95 | 0.85 | 83 |

[% ee$_R$] enantiomeric excess of (R) enantiomer in %

The data show that the Vfl transaminase converts Be3AP with high activity.

EXAMPLE 5

Optical Resolution of a Racemic Mixture of (R,S)-Cbz-3-aminopyrrolidine (C3AP) with *Vibrio fluvialis* Transaminase A 1.5 ml reaction vial was charged with:
10 μl of a (R,S)-C3AP solution in DMSO (5 mM final concentration)
20 μl pyridoxal phosphate, 10 mM (0.2 mM final concentration)
100 μl pyruvate, 100 mM (10 mM final concentration)
830 μl of a sodium phosphate buffer, 50 mM, pH 8

The reaction was started by the addition of 40 μl *Vibrio fluvialis*-transaminase. This corresponds to 7 U/ml. After 0 min, 10 min, 30 min and 60 min samples were taken.

Already after 10 min for (R)-C3AP an enantiomeric excess of (R) enantiomer of 97.3% ee$_R$ was determined in the sample. After 30 min no (S)-enantiomer could be detected.

EXAMPLE 6

Optical Resolution of a Racemic Mixture of (R,S)-1-N-boc-3-aminopiperidine (B3APi) with *Vibrio fluvialis* Transaminase A 1.5 ml reaction vial was charged with:
100 μl of a (R,S)-B3APi hydrochloride solution in water (5 mM final concentration)
20 μl pyridoxal phosphate, 10 mM (0.2 mM final concentration)
100 μl pyruvate, pH 8, 100 mM (10 mM final concentration)
580 μl of a sodium phosphate buffer, 50 mM, pH 8

The reaction was started by the addition of 200 μl *Vibrio fluvialis*-transaminase. This corresponds to 35 U/ml. After 10 min, 30 min, 60 min, 2 hrs, 4 hrs and 18 hrs samples were taken.

After 4 hrs an enantiomeric excess of 96.3% ee$_S$ was achieved. The conversion was 55±5%. Although it was necessary to use a large amount of the enzyme it could be shown that *Vibrio fluvialis* transaminase can be used for the optical resolution of (R,S)-B3APi.

What is claimed is:

1. A process for the preparation of an optically active chiral amine comprising:
a) providing an amino acceptor and a racemic mixture of 3-aminopyrrolidine (3AP) protected with a protective group at the ring nitrogen atom (1-N);
b) reacting the amino acceptor and the racemic mixture of 3AP protected with a protective group at the 1-N with an isolated (S)-selective transaminase which transfers the primary amino group at position 3 of AP to the amino acceptor, wherein the isolated (S)-selective transaminase being from *Vibrio fluviales, Alcaligenes denitrificans, Klebsiella pneumoniae* or *Bacillus thuringiensis*, thereby forming a reaction mixture; and c) producing an optically active chiral (R)-3AP, an amino product and a ketone product in the reaction mixture, wherein the protective group is benzyl, tert-butoxycarbonyl (Boc) or carbobenzoxy (Cbz).

2. The process according to claim 1, wherein the amino acceptor is selected from the group consisting of phenylpyruvic acid, pyruvic acid, glyoxylic acid, acetophenone, 2-ketoglutaric acid, acetone, 3-oxobutyric acid, 2-butanone, 3-oxopyrrolidine (3-OP), (3-pyridyl)methylketone (3-PMK), 3-oxobutyric acid ethyl ester (3-OBEE), 3-oxopentanoic acid methyl ester (3-OPME), salts thereof and combinations thereof.

3. The process according to claim 1, wherein the produced amino product is a primary amine or an amino acid.

4. The process according to claim 1, further comprising step d) removing from the reaction mixture at least one of the amino product and ketone product produced in step c).

5. The process according to claim 1, wherein removing from the reaction mixture at least one of the amino product and ketone product comprises adding an enzyme to the at least one of the amino product and ketone product, spontaneously decarboxylating the at least one of the amino product and ketone product, extracting the at least one of the amino product and ketone product or evaporating the at least one of the amino product and ketone product.

6. The process according to claim 5, wherein the enzyme used in step d) is a decarboxylase, a synthase or a dehydrogenase.

7. The process according to of claim 6, wherein the dehydrogenase is an alcohol dehydrogenase (ADH).

8. The process according to claim 4, wherein the amino product produced in step c) is removed in step d).

9. The process according to claim 4, further comprises removing the protective group at 1-N of 3AP produced in step c) or d) by a deprotection method.

10. The process according to claim 9, wherein the deprotection method comprises adding HCl and acetone to 1-N-protected 3AP protected with tert-butoxycarbonyl.

11. The process according to claim 4, wherein the optically active chiral (R)-3AP produced in the reaction mixture in step c) or d) has an optical purity of at least 70% of the total racemic mixture of 3AP in the reaction mixture at step c) or d).

12. The process according to claim 11, wherein the optically active chiral (R)-3AP present in the reaction mixture in step c) or d) has an optical purity of at least 90% of the total racemic mixture of 3AP in the reaction mixture at step c) or d).

13. The process according to claim 12, wherein the optically active chiral (R)-3AP present in the reaction mixture in step c) or d) has an optical purity of at least 99.9% of the total racemic mixture of 3AP in the reaction mixture at step c) or d).

14. The process according to claim 1, wherein reacting the amino acceptor and the racemic mixture of the amine with an (S)-selective transaminase comprises reacting the amino acceptor and the racemic mixture of 3AP with (S)-selective transaminase at a pH ranging from 5 to 9 in a buffer.

\* \* \* \* \*